(12) United States Patent
Bastaki

(10) Patent No.: US 10,039,738 B2
(45) Date of Patent: Aug. 7, 2018

(54) ULCER TREATMENT

(71) Applicant: United Arab Emirates University, Al-Ain (AE)

(72) Inventor: Salim M. A. Bastaki, Al-Ain (AE)

(73) Assignee: United Arab Emirates University, Al-Ain (AE)

( * ) Notice: Subject to any disclaimer, the term of this patent is extended or adjusted under 35 U.S.C. 154(b) by 0 days.

(21) Appl. No.: 14/143,079

(22) Filed: Dec. 30, 2013

(65) Prior Publication Data

US 2015/0182492 A1    Jul. 2, 2015

(51) Int. Cl.
*A61K 31/352* (2006.01)
*A61K 31/10* (2006.01)
*A61K 31/105* (2006.01)

(52) U.S. Cl.
CPC ............ *A61K 31/352* (2013.01); *A61K 31/10* (2013.01); *A61K 31/105* (2013.01)

(58) Field of Classification Search
CPC ..... A61K 31/352; A61K 31/10; A61K 31/105
See application file for complete search history.

(56) References Cited

PUBLICATIONS

Mayo Clinic (http://www.mayoclinic.org/diseases-conditions/peptic-ulcer/basics/causes/con-20028643?p=1, accessed Apr. 15, 2015).*
Elsom et al (Microbial Ecology in Health and Disease 2000; 12: 81-84).*
Walsh et al (The New England Journal of Medicine, 1995, 333(15):984-991).*
O'Gara et al (Applied and Environmental Microbiology, May 2000, p. 2269-2273).*
Khosla et al (Phytotherapy Research, Phytother. Res. 18, 87-91 (2004)).*
Cho et al (Life Sciences (1992) vol. 51, Issue 24, 1833-1842).*
Kahraman et al (Toxicology 183 (2003) 133-142).*
Pedraza-Chaverri et al (Molecular and Cellular Biochemistry 254: 125-130, 2003).*
Grudzinski et al (Phytomedicine, vol. 8(3), pp. 174-177).*
Naheed Amir et al., "Comparative effect of garlic (*Allium sativum*), onion (*Allium cepa*), and black seed (*Nigella sativa*) on gastric acid secretion and gastric ulcer" Research and Reports in Medicinal Chemistry, 2011, vol. 1, pp. 3-9.
Eric Block, "The Chemistry of Garlic and Onions." Enzyme-Substrate Complex, 1985, pp. 114-119.
P. Khosla et al., "Effect of Garlic Oil on Ethanol induced Gastric Ulcers in Rats." Phytotherapy Research, 2004, vol. 18, pp. 87-91.
Sisodia et al., "Gastric Antiulcer Activity of Rutin and Quercetin," The Indian Pharmacist, Jan. 2005, pp. 89-91.
Jappe, Uta, et al., "Garlic-Related Dermatoses: Case Report and Review of the Literature." American Journal of Contact Dermatitis, Mar. 1999, vol. 10, No. 1, pp. 37-39.

(Continued)

*Primary Examiner* — Angela C Brown-Pettigrew
(74) *Attorney, Agent, or Firm* — Fitch, Even, Tabin & Flannery LLP

(57) ABSTRACT

The present invention relates to the treatment of peptic ulcers. In particular, the present invention provides methods and compositions for the treatment of peptic ulcers. In addition, the present invention provides a method of reducing gastric acid secretion in a subject.

9 Claims, 6 Drawing Sheets

(56) References Cited

PUBLICATIONS

J. G. Chung et al. "Effects of Garlic Compounds Diallyl Sulfide and Diallyl Disulfide on Arylamine N-Acetyltransferase Activity in Strains of Helicobacter pylori from Peptic Ulcer Patients." American Journal of Chinese Medicine, Jun. 3, 1998, vol. XXVI, Nos. 3-4, pp. 353-364.

M. Shakeerabanu et al. "The Defensive Effect of Quercetin on Indomethacin Induced Gastric Damage in Rats." Advances in Biological Research, 2011, vol. 5, No. 1, pp. 64-70.

Y. Suzuki et al. "Anti-ulcer Effects of Antioxidants, Quercetin, α-Tocopherol, Nifedipine and Tetracycline in Rats." Jpn. J. Pharmacol, 1998, vol. 78, pp. 435-441.

J. Jappe et al. "Garlic-related Dermatoses: Case Report and Review of the Literature." Am J Contact Dermat. Mar. 1999, vol. 10, No. 1, (Abstract only).

E. A. O'Gara et al. "Activites of Garlic Oil, Garlic Powder, and Their Diallyl Constituents against Helicobacter pylori." Applied and Environmental Microbiology, May 2000, vol. 66, No. 5, pp. 2269-2273.

International Search Report and Written Opinion, International Patent Application No. PCT/162014/067389, dated Mar. 10, 2015, 10 pages.

N. Amir et al. "Comparative Effect of Garlic (*Allium sativum*), Onion (*Allium cepa*), and Black Seed (*Nigella sativa*) on Gastric Acid Secretion and Gastric Ulcer." Research and Reports in Medicinal Chemistry, Nov. 28, 2011, pp. 3-9.

L. Lawson et al. "Identification and HPLC Quantitation of the Sulfides and Dialk(en)yl Thiosulfinates in Commercial Garlic Products." Planta Med., 1991, vol. 57, pp. 363-370.

Emily A. Wilson and Barbara Demmig-Adams. "Antioxidant, anti-inflammatory, and anti microbial properties of garlic and onions", Nutrition & Food Science, 2007, vol. 37, issue 3, pp. 178-183.

\* cited by examiner

ULCER TREATMENT

FIELD OF INVENTION

The present invention relates to the treatment of peptic ulcers. In particular, the present invention provides methods and compositions for the treatment of peptic ulcers. In addition, the present invention provides a method of reducing gastric acid secretion in a subject.

BACKGROUND

Peptic ulcers are one of the most prevalent gastrointestinal disorders. They are caused by a number of factors including *Heliobacter pylori* infection, certain pharmaceuticals such as non-steroidal anti-inflammatory drugs (NSAIDs), stress and diet.

Typical treatments include administration of antibiotics together with proton pump inhibitors or $H_2$-receptor antagonists, which help to raise the gastrointestinal pH level by inhibiting gastric acid secretion. However, existing treatments can have deleterious side effects. Therefore, there remains a need to provide improved methods of treatment and prevention of these conditions.

Garlic (*Allium sativum*) and onion (*Allium cepa*) are among the oldest of all cultivated plants and have important dietary and medicinal roles (Block, 1985). Khosla and co-workers have shown garlic oil to be protective against ethanol-induced gastric ulcers in rats (Khosla et al., 2004). The protective roles of raw and boiled garlic and onion extracts against ethanol-induced gastric ulcers and gastric acid secretion was previously investigated by the present inventors (Amir et al., 2011).

SUMMARY OF INVENTION

In a first aspect, the present invention provides a method of treating or preventing peptic ulcers comprising administering to a subject a therapeutically effective amount of at least one of allyl sulphide, allyl disulphide, quercetin and a combination thereof.

Preferably, the active compound (allyl sulphide, allyl disulphide, quercetin or a combination thereof) is administered alone or in combination with one or more pharmaceutically acceptable carriers or excipients.

In one preferred embodiment, the active compound is allyl sulphide. In another preferred embodiment, the active compound is allyl disulphide. In yet a further preferred embodiment, the active compound is quercetin.

Preferably, the subject is a mammal. More preferably, the subject is a human.

Administration may be carried out by any suitable route. In preferred embodiments, the administration is carried out via the oral route.

Preferably the therapeutically effective amount ranges from about 10 mg per kg body weight (mg/kg) to about 100 mg/kg, and preferably from about 30 mg/kg to about 80 mg/kg, and more preferably, from about 40 mg/kg to about 60 mg/kg and still more preferably about 50 mg/kg. In certain embodiments, the therapeutically effective amount is 10, 20, 30, 40, 50, 60, 70, 80, 90, or 100 mg per kg body weight.

In a particularly preferred embodiment, allyl sulphide is administered orally at 50 mg per kg body weight. In another particularly preferred embodiment, allyl disulphide is administered orally at 10 mg per kg body weight. In a final particularly preferred embodiment, quercetin is administered orally at 50 mg per kg body weight.

In a second aspect, the present invention provides method of reducing gastric acid secretion in a subject, the method comprising administering a therapeutically effective amount of at least one of allyl sulphide, allyl disulphide, quercetin and a combination thereof.

Preferably, the active compound (allyl sulphide, allyl disulphide, quercetin or a combination thereof) is administered alone or in combination with one or more pharmaceutically acceptable carriers or excipients.

In one preferred embodiment, the active compound is allyl sulphide. In another preferred embodiment, the active compound is allyl disulphide. In yet a further preferred embodiment, the active compound is quercetin.

Preferably, the subject is a mammal. More preferably, the subject is a human.

Administration may be carried out by any suitable route. In preferred embodiments, the administration is carried out via the oral route.

Preferably the therapeutically effective amount ranges from about 10 mg per kg body weight (mg/kg) to about 100 mg/kg, and preferably from about 30 mg/kg to about 80 mg/kg, and more preferably, from about 40 mg/kg to about 60 mg/kg and still more preferably about 50 mg/kg. In certain embodiments, the therapeutically effective amount is 10, 20, 30, 40, 50, 60, 70, 80, 90, or 100 mg per kg body weight.

In a particularly preferred embodiment, allyl sulphide is administered orally at 50 mg per kg body weight. In another particularly preferred embodiment, allyl disulphide is administered orally at 10 mg per kg body weight. In a final particularly preferred embodiment, quercetin is administered orally at 50 mg per kg body weight.

In a further aspect, there is provided allyl sulphide for use in the treatment of peptic ulcers.

In yet a further aspect, there is provided allyl disulphide for use in the treatment of peptic ulcers.

In a still further aspect, there is provided quercetin for use in the treatment of peptic ulcers.

DESCRIPTION OF DRAWINGS

The present invention will be further understood by reference to the attached drawings, in which.

DETAILED DESCRIPTION

Figure 1:
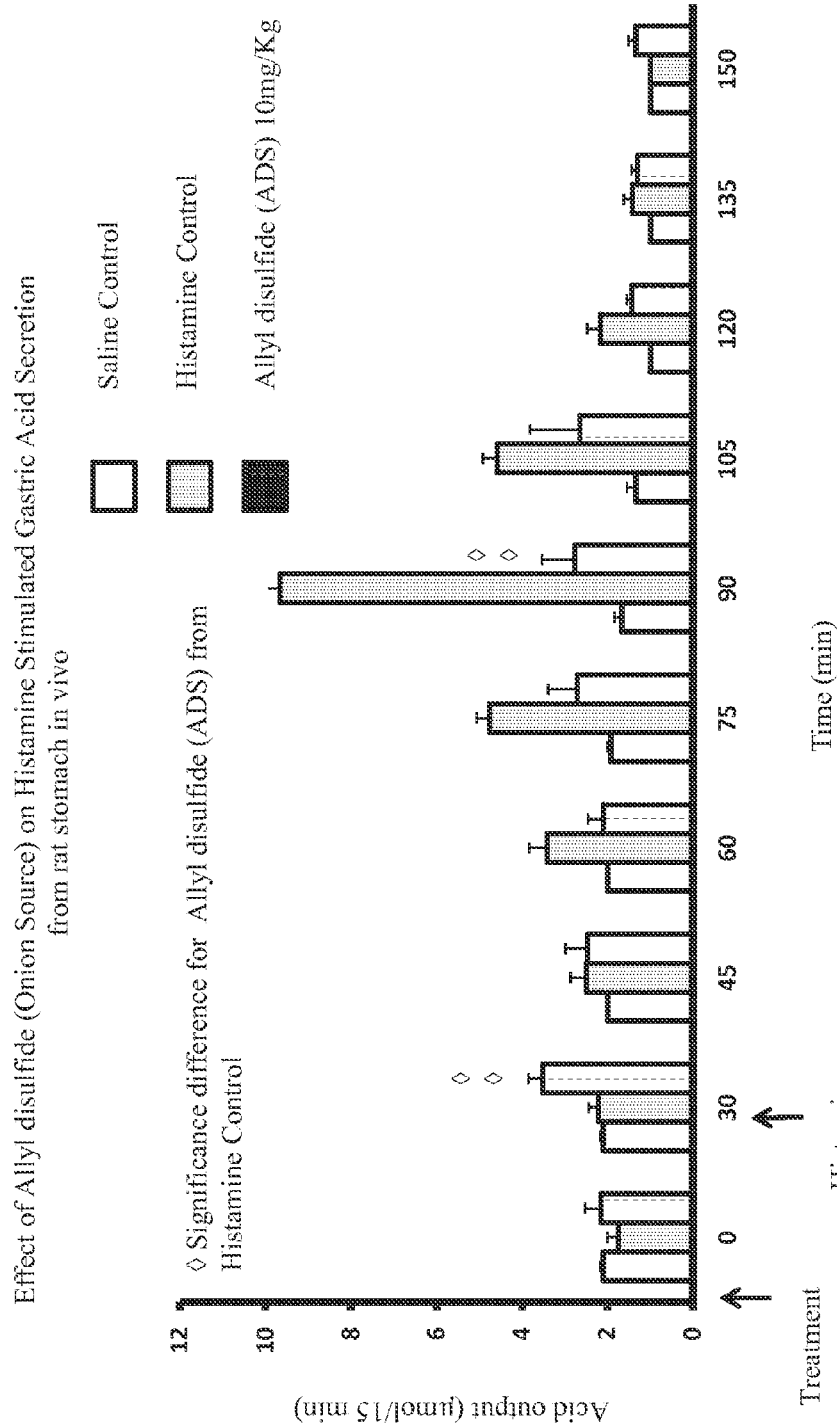
FIG. 1 shows the effect of allyl disulfide (onion source) on histamine stimulated gastric acid secretion from rat stomach in vivo.

Although onion and garlic extracts have previously been shown by the present inventors to have a protective effect against ethanol-induced gastric ulcers in vivo, the specific active compounds responsible for this effect have not been identified until now. Onion and garlic both contain a host of potentially biologically active compounds, some of which may have undesirable effects, including but not limited to unpleasant odours or tastes. Furthermore, though plant extracts may be safer than synthetic chemicals in certain circumstances, they are not as easily standardized and therefore it may be more difficult to obtain regulatory clearance for such extracts. Administration of specific active compounds at controlled doses is therefore advantageous over the use of plant extracts.

The present invention provides a method of treating or preventing peptic ulcers comprising administering to a subject a therapeutically effective amount of allyl sulphide, allyl disulphide, quercetin or a combination thereof.

The term "peptic ulcer" is generally intended to mean any ulcer of the gastrointestinal tract. These may include ulcers of the stomach (also termed gastric ulcers), duodenum, jejunum (also termed middle intestine or mid-gut), ileum or cecum. Ulcers arise due to a number of factors including Heliobacter pylori infection, certain pharmaceuticals such as non-steroidal anti-inflammatory drugs (NSAIDs), stress and diet. In the present application the term peptic ulcer is intended to encompass ulcers due to any cause.

The present invention also provides a method of reducing gastric acid secretion in a subject, the method comprising administering an effective amount of allyl sulphide, allyl disulphide, quercetin or a combination thereof.

The phrase "reducing stomach acid secretion" refers to a lowering of acid output by the cells lining the stomach.

Allyl sulphide, also referred to as allyl sulfide, diallyl sulphide or diallyl sulfide, is an organosulfur compound derived from some members of the Allium family, such as onion (*Allium cepa*). It is commercially available from a number of suppliers.

Allyl disulphide, also referred to as allyl disulfide, diallyl disulphide or diallyl disulfide, is an organosulfur compound derived from garlic and some other members of the Allium family. It is commercially available from a number of suppliers.

Quercetin is a plant-derived flavonoid found in a number of different plant groups, including members of the Allium family. It is commercially available from a number of suppliers.

Preferably, the subject is a mammal. More preferably, the subject is a human.

In preferred embodiments, the administration is carried out via the oral route. Preferably the therapeutically effective amount ranges from about 10 mg per kg body weight (mg/kg) to about 100 mg/kg, and preferably from about 30 mg/kg to about 80 mg/kg, and more preferably, from about 40 mg/kg to about 60 mg/kg and still more preferably about 50 mg/kg. In certain embodiments, the therapeutically effective amount is 10, 20, 30, 40, 50, 60, 70, 80, 90, or 100 mg per kg body weight.

In a further aspect, there is provided allyl sulphide for use in the treatment of peptic ulcers.

In yet a further aspect, there is provided allyl disulphide for use in the treatment of peptic ulcers.

In a still further aspect, there is provided quercetin for use in the treatment of peptic ulcers.

Allyl sulphide, allyl disulphide, quercetin are all naturally derived compounds and are expected to be well tolerated in vivo, with few or no deleterious side effects.

The invention will be further understood by reference to the following non-limiting example.

EXAMPLES

Materials and Methods

Male Wistar rats (weighing 200-225 g) were fasted for 24 hours in wire mesh cages to avoid coprophagy. The rats were obtained from the animal facilities of the Faculty of Medicine and Health Sciences of the United Arab Emirates (UAE) University.

Materials

Onion and garlic compounds (Quercetin, Cat # Q4951, Diallyl sulfide, Cat # A35801, Allyl disulfide, Cat# W202800) were obtained from the from Sigma-Aldrich Chemical Company (Sigma Chemical Co., St. Louis, Mo., USA). Hydrochloric acid (HCl), ethanol, and histamine were obtained from Sigma (St Louis, Mo.).

Example 1—Gastric Acid Secretion Measured In Vivo

Groups of six rats were used for the experiment. Rats were initially anesthetized with urethane (1.5 g/kg) intraperitoneally. Following general anesthesia, a laparotomy was immediately performed followed by the insertion of a polyethylene tube at the pyloric end of the stomach. This tube was used to collect exudates from the stomach. An orogastric tube was inserted in the stomach via the esophagus. This tube was used to perfuse the stomach with saline (pH 7) at a constant rate of 7 mL/min at 37° C. Following perfusion, effluent samples were collected and titrated against 0.01 M NaOH every 15 minutes for acid secretion. After basal acid output for 1 hour, either saline, quercetin (50 mg/kg,), or diallyl sulfide (50 mg/kg), or allyl disulfide (10 mg/kg) at neutral pH was given orally and 30 minutes later, histamine (2 mg/kg) was administered as a bolus injection. Acid output was monitored continuously for 2 hours thereafter. The acid output was calculated and expressed as $\mu mol$ ($15\ min^{-1}$). This study had an ethical clearance from the Ethical Committee of the UAE University.

Results

Figure 2:
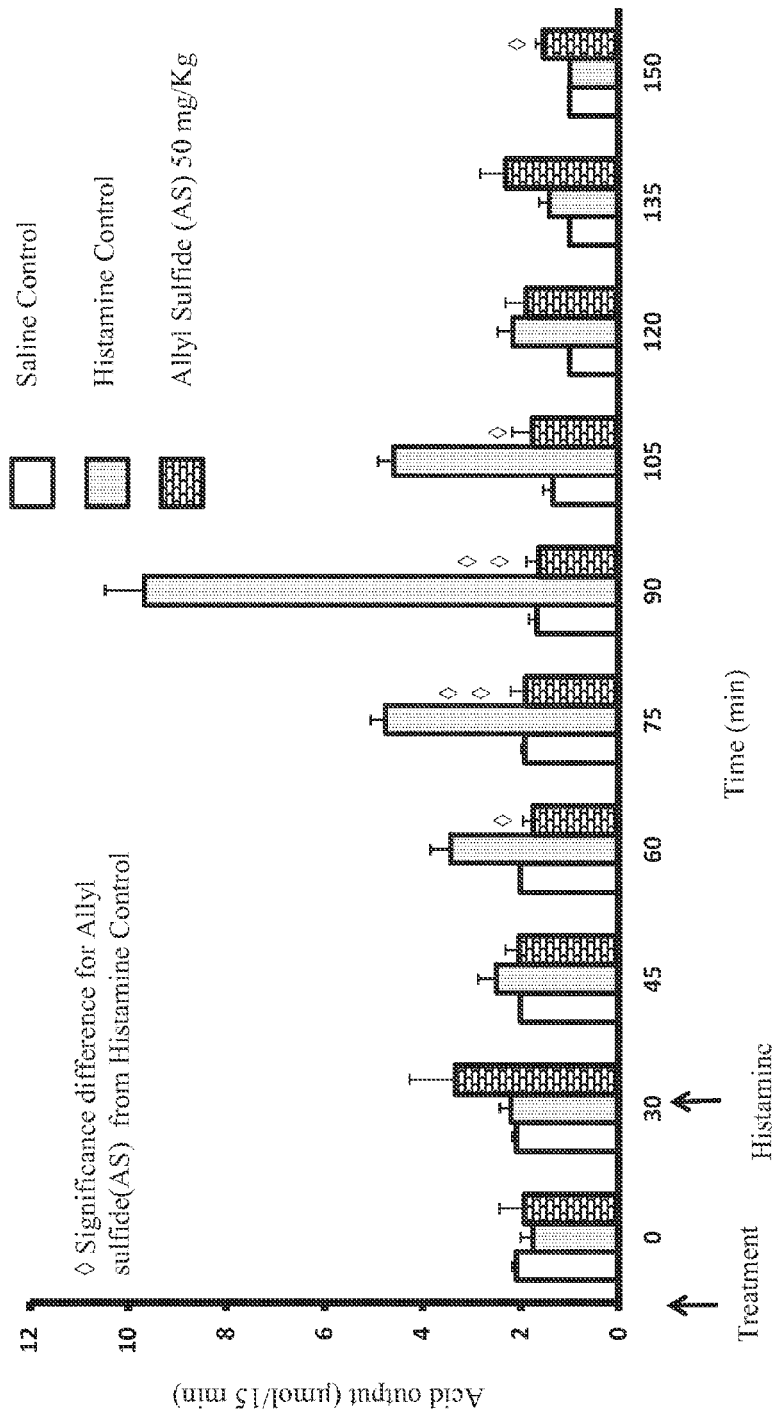
FIG. 2 shows the effect of allyl sulfide (garlic source) on histamine stimulated gastric acid secretion from rat stomach in vivo.
Figure 3:
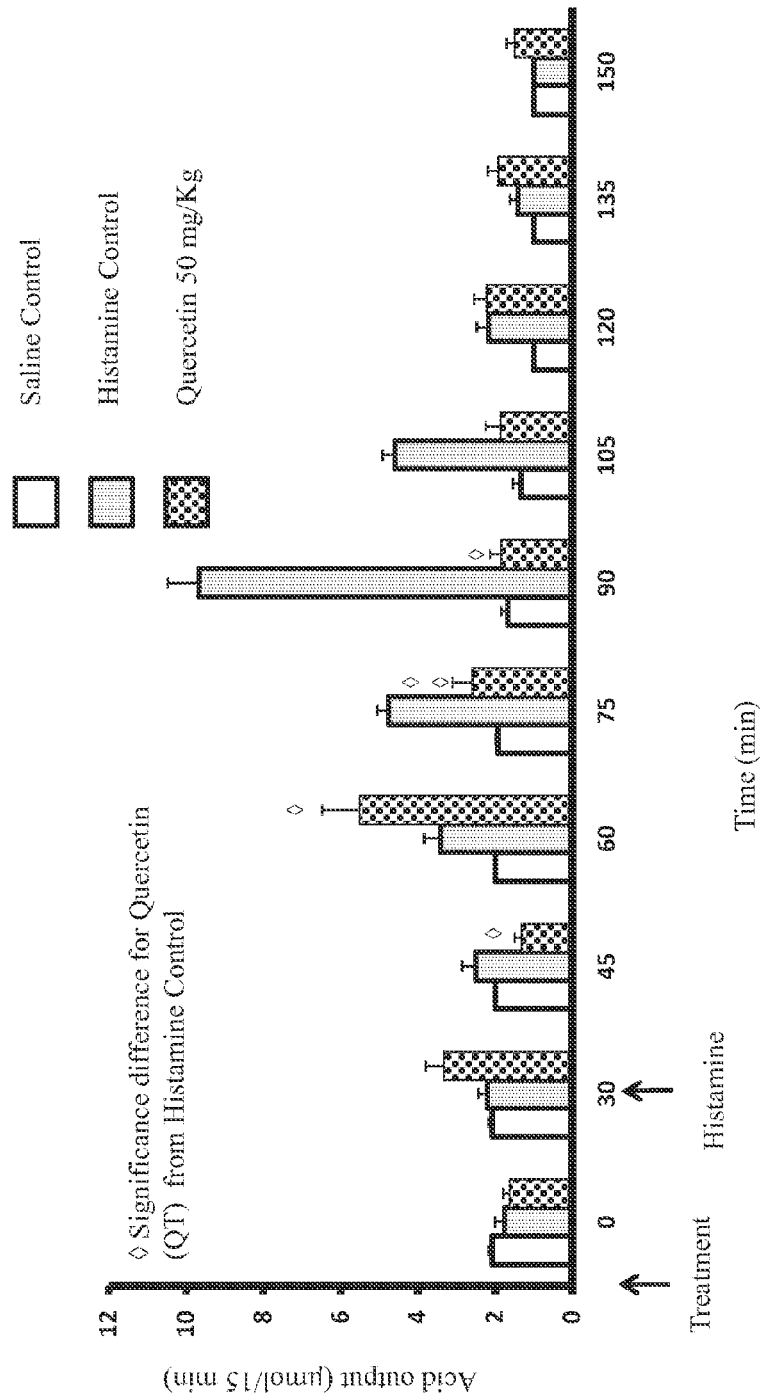
FIG. 3 shows the effect of quercetin (onion source) on histamine stimulated gastric acid secretion from rat stomach in vivo.

The results of the in vivo gastric acid secretion tests are shown in table 1. FIGS. 1, 2 and 3 show the effect of allyl disulfide (onion source), allyl sulphide (garlic source) and quercetin (onion source), respectively, on histamine stimulated gastric acid secretion from rat stomach in vivo.

As can be seen from the figures, rats treated with allyl disulfide, allyl sulphide or quercetin and then challenged with histamine show reduced acid output compared to the histamine control.

TABLE 1

| | | Results of in vivo acid secretion test | | | | | | | | | |
|---|---|---|---|---|---|---|---|---|---|---|---|
| | | Time (min) | | | | | | | | | |
| Group | | 0 | 30 | 45 | 60 | 75 | 90 | 105 | 120 | 135 | 150 |
| Control | Mean | 1.75 | 2.2 | 2.45 | 3.162 | 4.448 | 7.891 | 3.97 | 1.85 | 1.362 | 1.005 |
| | N | 6 | 6 | 6 | 6 | 6 | 6 | 6 | 6 | 6 | 6 |
| | Std. | 0.612 | 0.566 | 0.903 | 1.175 | 1.141 | 3.584 | 1.512 | 0.731 | 0.428 | 0.012 |

TABLE 1-continued

Results of in vivo acid secretion test

| Group | | 0 | 30 | 45 | 60 | Time (min) 75 | 90 | 105 | 120 | 135 | 150 |
|---|---|---|---|---|---|---|---|---|---|---|---|
| | Std. Dev. Error | 0.25 | 0.231 | 0.369 | 0.48 | 0.466 | 1.463 | 0.617 | 0.298 | 0.175 | 0.005 |
| Allyl di sulfide 10 mg/kg | Mean | 2.154 | 3.514 | 2.458 | 2.085 | 2.701 | 2.77 | 2.648 | 1.431 | 1.286 | 1.34 |
| | N | 7 | 7 | 7 | 7 | 7 | 7 | 7 | 7 | 7 | 7 |
| | Std. Dev. | 0.989 | 0.871 | 1.384 | 0.94 | 1.811 | 2.018 | 3.081 | 0.294 | 0.368 | 0.452 |
| | Std. Error | 0.374 | 0.329 | 0.523 | 0.355 | 0.685 | 0.763 | 1.165 | 0.111 | 0.139 | 0.171 |
| Allyl sulfide 50 mg/kg | Mean | 1.926 | 3.328 | 2.023 | 1.742 | 1.901 | 1.627 | 1.761 | 1.883 | 2.301 | 1.525 |
| | N | 7 | 7 | 7 | 7 | 7 | 7 | 7 | 7 | 7 | 7 |
| | Std. Dev. | 1.345 | 2.491 | 0.74 | 0.548 | 0.796 | 0.677 | 1.069 | 1.11 | 1.384 | 0.453 |
| | Std. Error | 0.508 | 0.941 | 0.28 | 0.207 | 0.301 | 0.256 | 0.404 | 0.42 | 0.523 | 0.171 |
| Quercetin 50 mg/kg | Mean | 1.633 | 3.323 | 1.299 | 5.507 | 2.579 | 1.84 | 1.868 | 2.213 | 1.927 | 1.497 |
| | N | 6 | 6 | 6 | 6 | 6 | 6 | 6 | 6 | 6 | 6 |
| | Std. Dev. | 0.398 | 1.154 | 0.467 | 2.398 | 1.275 | 0.718 | 0.937 | 0.799 | 0.644 | 0.503 |
| | Std. Error | 0.162 | 0.471 | 0.19 | 0.979 | 0.521 | 0.293 | 0.383 | 0.326 | 0.263 | 0.206 |

Example 2—Antiulcer Activity

Rats were divided into groups of six to seven animals for each experiment. Each group received either neutral pH physiologic saline (1 mL) or water extract of either quercetin, diallyl sulfide or allyl disulfide (1 mg/kg, 10 mg/kg, 50 mg/kg or 100 mg/kg; six rats for each dose) by gastric gavage. Two additional comparison groups received either the proton pump inhibitor Lansoprazole (10 mg/kg) or the $H_2$-receptor antagonist Ranitidine (20 mg/kg). After 30 minutes of the treatment, 1 mL of acidified ethanol (60% ethanol with 150 mM HCl), an ulcerogenic agent, was administered orally to the animals. The animals were sacrificed 1 hour later by increasing the dose of the anaesthesia. The abdomen was incised, and the stomachs removed, cut open along the greater curvature, and rinsed with saline to remove any adherent particles and mucus. The open stomach was spread on a sheet of cork so as to have a clear view of gastric lesions in the gastric mucosa. The total lengths of hemorrhagic lesions, which were approximately 1 mm in length and formed in the glandular portion of the gastric mucosa, were taken as ulcer index. An observer who was unaware of the drug treatments confirmed the ulcer index. The percentage reduction of the ulcer index in the drug-treated groups was calculated from the saline treated groups. The use of 60% ethanol in 150 mM HCl to produce an ulcerogenic effect was based on earlier observation that ethanol 50% and over provided a reproducible model of gastric damage.

Results

Figure 4:
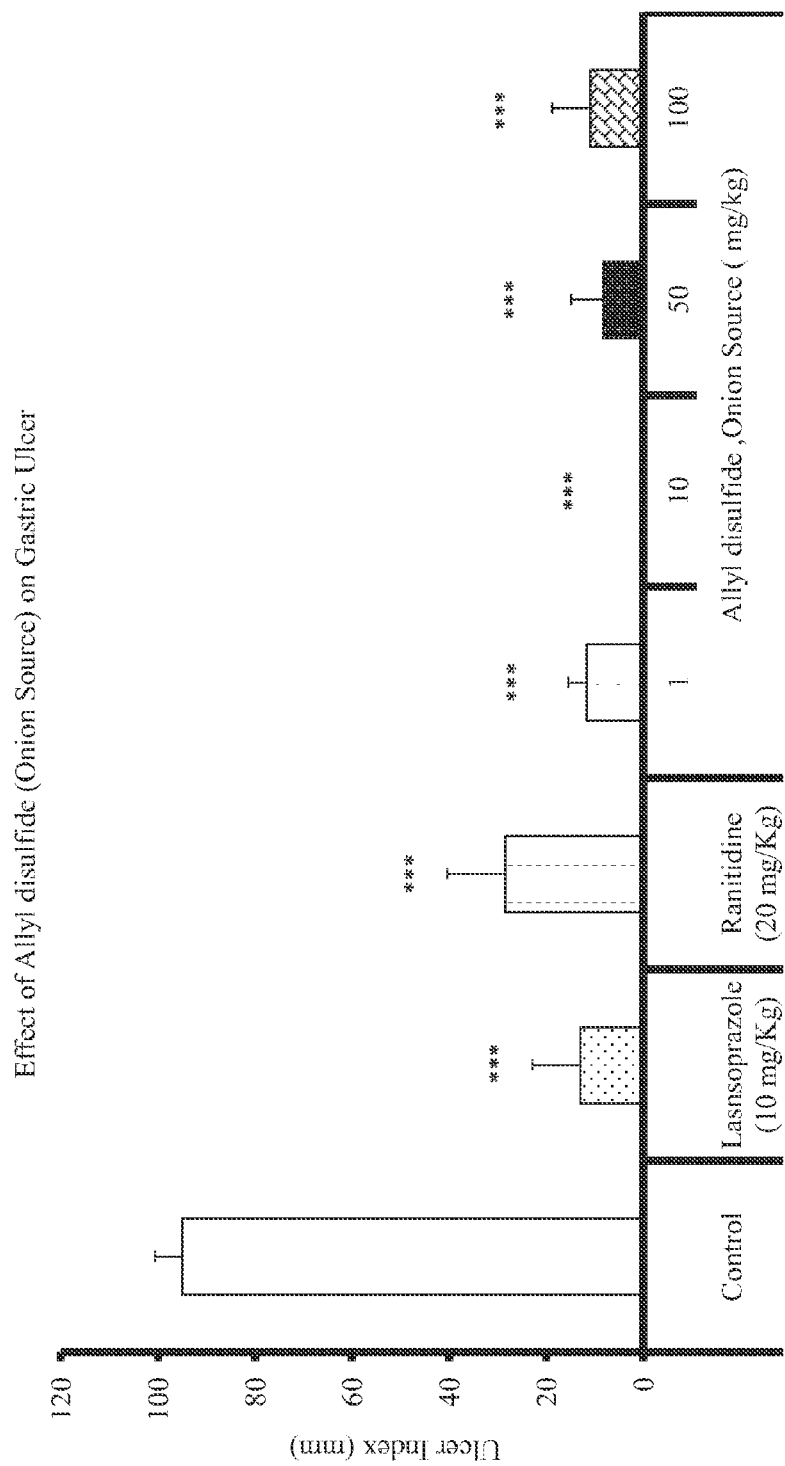
FIG. 4 shows the effect of allyl disulfide (onion source) on gastric ulcer formation in rat stomachs.
Figure 5:
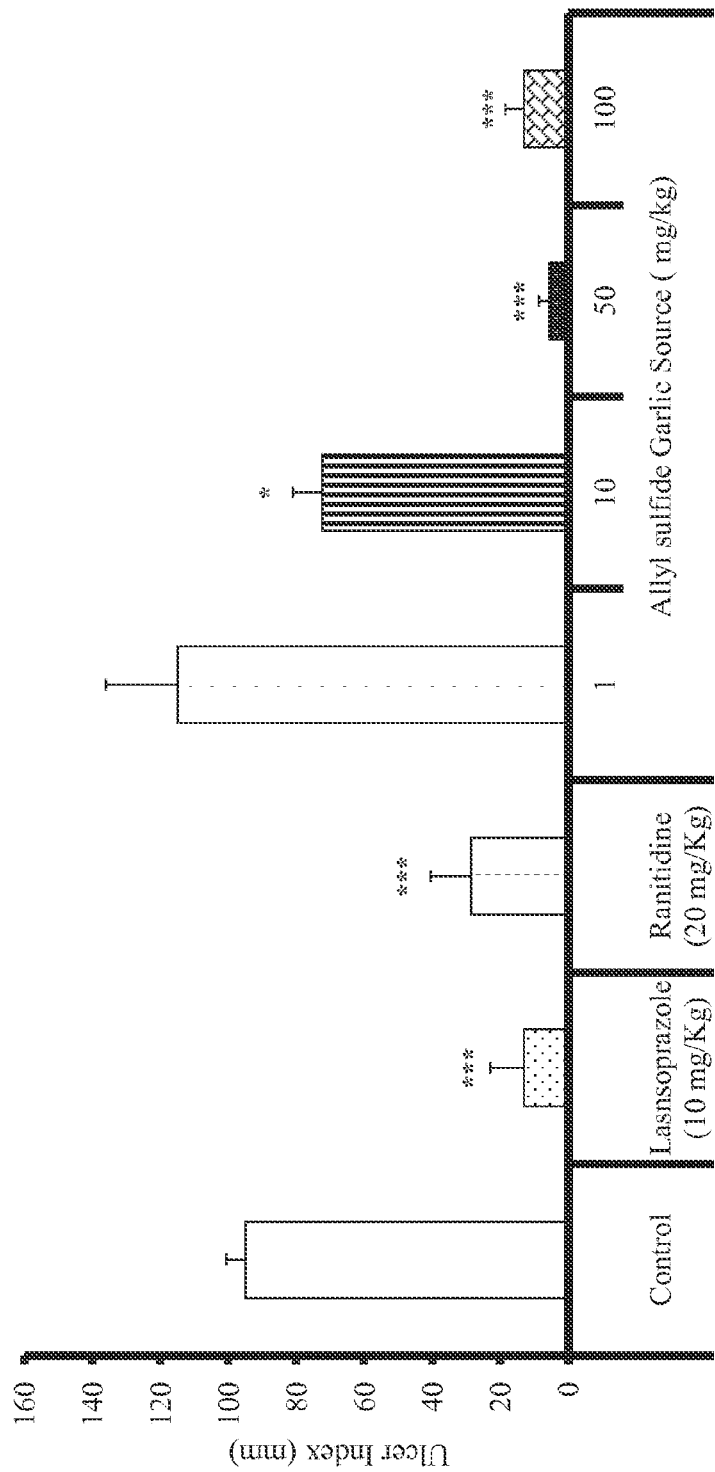
FIG. 5 shows the effect of allyl sulfide (garlic source) on gastric ulcer formation in rat stomachs.
Figure 6:
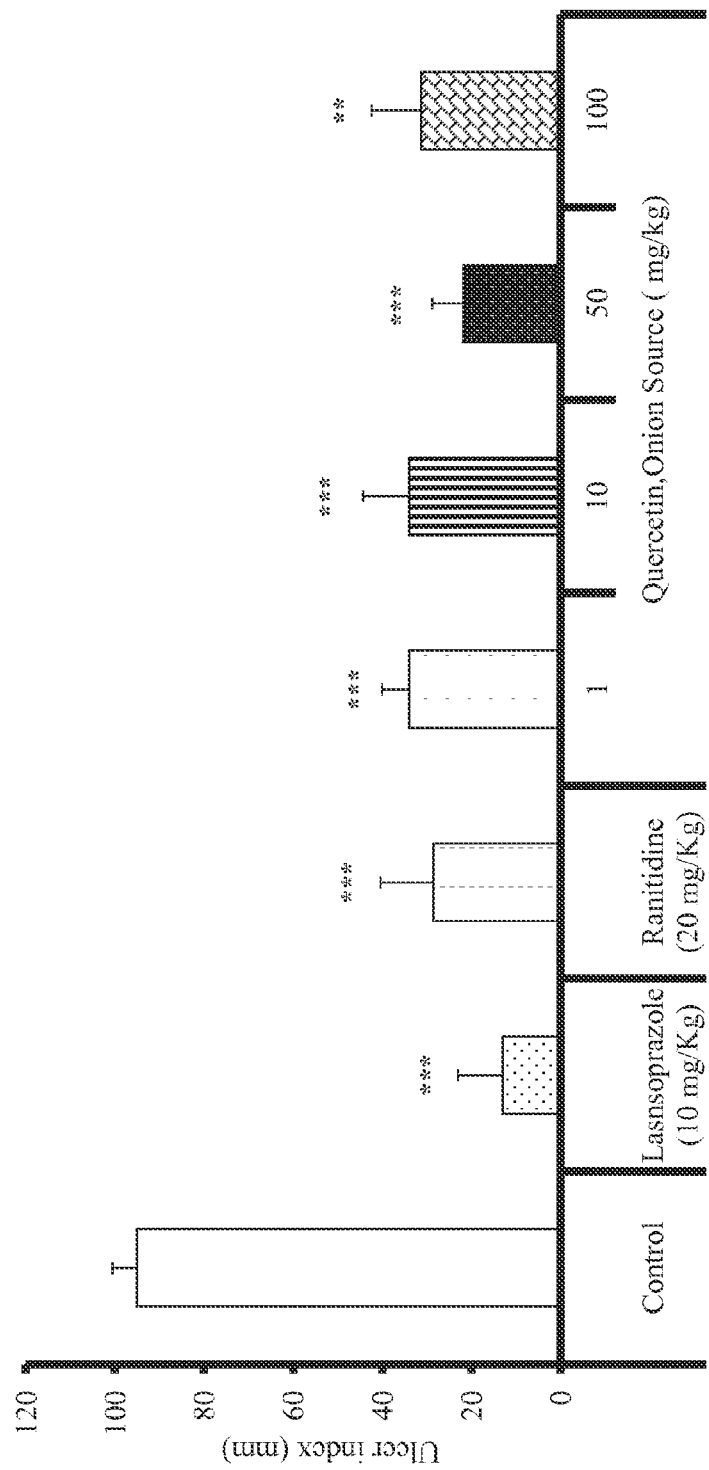
FIG. 6 shows the effect of quercetin (onion source) on gastric ulcer formation in rat stomachs.

The results of the antiulcer activity test are shown in table 2. FIGS. 4, 5 and 6 show the effect of allyl disulfide (onion source), allyl sulphide (garlic source) and quercetin (onion source), respectively, on gastric ulcer formation in the rat model.

Rats treated with either quercetin, diallyl sulfide or allyl disulfide show significantly reduced ulcer index compared to the control. The ulcer index is comparable to treatment with Lansoprazole or Ranitidine.

TABLE 2

Results of antiulcer test

| | | Ulcer Index | | | |
|---|---|---|---|---|---|
| Group | Dose (mg/kg) | Mean | N | Std. Deviation | Std. Error of Mean |
| Control | 0 | 95.00 | 7 | 14.84 | 5.61 |
| Lansoprazole | 10 | 13.00 | 6 | 24.31 | 9.93 |
| Ranitidine | 20 | 28.50 | 6 | 29.06 | 11.86 |
| Allyl sulfide (Garlic Source) | 1 | 114.83 | 6 | 51.91 | 21.19 |
| | 10 | 72.33 | 6 | 21.13 | 8.62 |
| | 50 | 5.50 | 6 | 7.48 | 3.05 |
| | 100 | 13.00 | 6 | 13.37 | 5.46 |
| Allyl disulfide (Onion Source) | 1 | 11.67 | 6 | 9.50 | 3.88 |
| | 10 | 0.00 | 6 | 0.00 | 0.00 |
| | 50 | 8.33 | 6 | 16.02 | 6.54 |
| | 100 | 11.00 | 6 | 19.19 | 7.84 |
| Quercetin (Onion Source) | 1 | 34.00 | 6 | 14.93 | 6.09 |
| | 10 | 34.00 | 6 | 25.09 | 10.24 |
| | 50 | 21.83 | 6 | 17.15 | 7.00 |
| | 100 | 31.17 | 6 | 27.45 | 11.21 |

While the invention has been described in detail and with reference to specific embodiments thereof, it will be apparent to one of skill in the art that various changes and modifications can be made therein without departing from the spirit and scope thereof. Moreover, all embodiments described herein are considered to be broadly applicable and combinable with any and all other consistent embodiments, as appropriate.

The disclosures of any and all publications cited herein are hereby incorporated by reference in their entireties.

REFERENCES

Amir N, Al Dhaheri A, Al Jaberi N, Al Marzouqi F, Bastaki S M A. Comparative effect of garlic (*Allium sativum*), onion (*Allium cepa*), and black seed (*Nigella sativa*) on gastric acid secretion and gastric ulcer. *Research and Reports in Medicinal Chemistry* 2011:1 3-9.

Block E. The chemistry of garlic and onion. *Sci Amer.* 1985; 252:114-119.

Khosla P, Karan R S, Bhargaya V K. Effect of garlic oil on ethanol-induced gastric ulcers in rats. *Phytother Res.* 2004; 18 (1):87-91.

The invention claimed is:

1. A method of treating peptic ulcers caused by at least one non-microbial factor, the method comprising administering to a subject in need thereof a therapeutically effective amount of at least one of allyl sulphide, allyl disulphide, and a combination thereof, wherein said at least one of allyl sulphide, allyl disulphide, and a combination thereof, is administered alone or in combination with one or more pharmaceutically acceptable carriers or excipients, wherein the therapeutically effective amount ranges from about 10 mg per kg body weight (mg/kg) to about 100 mg/kg.

2. The method of claim 1, wherein the subject is a mammal.

3. The method of claim 2, wherein the subject is a human.

4. The method of claim 1, wherein the administration is carried out via the oral route.

5. The method of claim 1, wherein the allyl sulphide is administered in a therapeutically effective amount of about 50 mg/kg.

6. The method of claim 1, wherein the allyl disulphide is administered in a therapeutically effective amount of about 10 mg/kg.

7. The method of claim 1, wherein the non-microbial factor is at least one of stress, diet, and administration of non-steroidal anti-inflammatory drugs.

8. The method of claim 1, wherein said peptic ulcers are in the form of stomach ulcers.

9. The method of claim 1, wherein the method includes administering to a subject a therapeutically effective amount of allyl sulphide, which is administered alone and not in combination with one or more pharmaceutically acceptable carriers or excipients nor in combination with any other active compound.

* * * * *